United States Patent [19]
Oertel et al.

[11] Patent Number: 6,001,861
[45] Date of Patent: Dec. 14, 1999

[54] USE OF PRAMIPEXOLE IN THE TREATMENT OF RESTLESS LEGS SYNDROME

[75] Inventors: Wolfgang H. Oertel, Ranschenberg; Dieter Meier, Weisbaden, both of Germany; Baltazar Gomez-Mancilla, Portage, Mich.; Jacques Montplaisir, Montreal, Canada

[73] Assignee: Pharmacia & Upjohn Company, Kalamzoo, Mich.

[21] Appl. No.: 09/008,212

[22] Filed: Jan. 16, 1998

[51] Int. Cl.⁶ .................................................. A61K 31/425
[52] U.S. Cl. ............................................................. 514/367
[58] Field of Search ............................................. 514/367

[56] References Cited

U.S. PATENT DOCUMENTS 5,112,842   5/1992   Zierenberg et al. .................... 514/367

FOREIGN PATENT DOCUMENTS

| 0186087 | 12/1985 | European Pat. Off. . |
| 3933738 | 10/1989 | Germany . |
| 3843227 | 7/1990 | Germany . |
| 94/13287 | 6/1994 | WIPO . |
| 96/18395 | 6/1996 | WIPO . |
| WO98/31362 | 7/1998 | WIPO . |

OTHER PUBLICATIONS

JE Ahlskog, et al., "Adjunctive Cabergoline Therapy of Parkinson's Disease: Comparison with Placebo and Assessment of Dose Response and Duration of Effect," Clin. Neuropharmacol, 1996; 19:202–212.

S Akpinar, "Restless Legs Syndrome Treatment with Dopaminergic Drugs," Clinical Neuropharmacology, 1987; 10:69–79.

RP Allen, et al., "Augmentation of the Restless Legs Syndrome with Carbidopa/Levodopa" Sleep, 1996; 19(3):205–13.

Anonymous Author, "My Doctor Prescribed Sinemet for my Restless Legs and it was a Catastrophe." Johns Hopkins Medical Letter, Health After 50, 1998; 10 (12) 8.

Anonymous Author, "Restless Legs Syndrome Often Not Recognized, May be Misdiagnosed," Geriatrics, 1998; 53(2): 101.

PM Becker, et al., "Dopaminergic Agents in Restless Legs Syndrome and Periodic Limb Movements of Sleep: Response and Complications of Extended Treatment in 49 Cases," 1993; Sleep, 16(8); pp. 713–716.

D Boghen, et. al., "The Treatment of Restless legs Syndrome with Clonazepam: A Prospective Controlled Study," Can J Neurol Sci, 1986; 13:245–247.

B Bornstein, "Restless Legs," Psychiat Neurol, 1961; 141:165–201.1.

C Brodeur, et. al., "Treatment of RLS and PMS with L–dopa: A Double–blind Controlled Study," Neurology, 1988; 35:1845–1848.

N Callaghan, "Restless Legs Syndrome in uremic Neuropathy," Neurology, 1966; 16:359–361.

RM Coleman, "Periodic Movements in Sleep (Nocturnal Myoclonus) and Restless Legs Syndrome." In: Guilleminault C, (ed) Sleeping and Walking Disorders: Indications and Techniques, 1982; Menlo Park: Addison Wesley; 265–295.

V Collado–Seidel, et al., "A Controlled Study of Additional sr–L–dopa in L–dopa–Responsive Restless Legs Syndrome with Late–Night Symptoms," Neurology, 1999; 52:285–290.

CJ Earley, et al., "Pergolide and Carbidopa/Levodopa Treatment of the Restless Legs Syndrome and Periodic Leg Movements in Sleep in a Consecutive Series of Patients," Sleep 1996; 19(10):801–10.

KA Ekbom, "Restless Legs," Acta Medica Scandinavica, 1945; suppl. 158:1–123.

KA Ekbom, "Restless Legs Syndrome," Neurology, 1960; 10:868–873.

RG Fariello, "Pharmacodynamic and Pharmacokinetic Features of Carbergoline," Drugs, 1997; 55:S2, 10–16.

A Feigen, "Restless Legs Syndrome," JAMA, 1995; 274 (15) 1191–2.

B Frankel, "Restless Legs Syndrome," JAMA, 1974; 230:1302–1303.

LI Golbe, "Pregnancy and Movement Disorders," Neurologic Clinics, 1994; 12/3 (497–508).

C Gorman, et al., "Symptoms of Restless Legs," Arch Intern Med, 1965; 115:155–60.

C Guilleminault, et al., "Dopaminergic Treatment of Restless Legs and Rebound Phenomenon," Neurology, 1993; 43(2):445.

D Harriman, et al., "Ekbom's Syndrome and Burning Paraesthesiae," Brain, 1970; 93:393–406.

EM Heiman, et al., "Lithium–aggravated Nocturnal Myoclonus and Restless Legs Syndrome [letter]," American Journal of Psychiatry, 1986; 143:1191–1192.

F Heinze, et al., "Restless Legs and Orthostatic Hypotension in Primary Amyloidosis," Arch Neurol, 1967; 16:497–500.

W Hening, et al., "The Cortical Premovement Potentials in RLS Jerks," Sleep Res, 1991; 20:255.

WA Hening, et. al., "Dyskinesias while awake and periodic movements in Sleep in Restless Legs Syndrome: Treatment with Opioids," Neurology; 1986; 36:1363–1366.

S Iannaccone, et al., "Evidence of Peripheral Axonal Neuropathy in Primary Restless Legs Syndrome," Movement Disorders, 1995; 10:2–9.

S Jorgensen, et al., "Restless Legs Syndrome,"—Abstract, Ugeskrift for Laeger, 1989; 151 (11) 670–1.

PW Kaplan, et al., "A Double–Blind, Placebo–Controlled Study of the Treatment of Periodic Limb Movements in Sleep using Carbidopal/Levodopa and Propoxyphene," Sleep, 1993; 16 (8) 717–23.

S Kotagal, et al., "Nocturnal Myoclonus—A Sleep Disturbance in Children with Leukemia," Annals of Neurology, 1984; 16:392.

(List continued on next page.)

Primary Examiner—Phyllis G. Spivack
Attorney, Agent, or Firm—Thomas A. Wootton

[57]   ABSTRACT

The present invention provides the use of pramipexole in the treatment of restless legs syndrome.

4 Claims, No Drawings

OTHER PUBLICATIONS

E Lugaresi, et al., "*Nocturnal Myoclonus and Restless Legs Syndrome,*" In: S Fahn et al. (eds), Advances in Neurology, 1986; vol. 43: Myoclonus, New York: Raven Press; 295–307.

MW Mahowald, et al., "*Parasomnias Including in the Restless Legs Syndrome,*" Clinics in Chest Medicine, 1998; 19/1 (183–202).

P Martinelli, et al., "*Nocturnal Myoclonus, Restless Legs Syndrome, and Abnormal Electrophysiological Findings,*" Ann Neurol, 1987; 21:515.

WB Matthews, "*Iron Deficiency and Restless Legs,*" Br Med J, 1976; 1–898.

M Miyagi, et al., "*Dopamine Receptor Affinities in vitro and Steriotypic Activities in vivo of Cabergoline in Rats,*" Biol. Pharm. Bull., 1996; 19L 1210–1213.

H Moldofsky, et al., "*Sleep–related Myoclonus in Rheumatic Pain Modulation Disorder (Fibrositis Syndrome) and in Excessive Daytime Somnolence,*" Psychosomatic Medicine, 1984; 46:145–151.

J Montplaisir, et al., "*Familial Restless Legs with Periodic Movements in Sleep:Electrophysiological, Biochemical, and Pharmacological Study,*" Neurology, 1985; 35:130–134.

J Montplaisir, et. al., "*Restless Legs Syndrome and Periodic Movements in Sleep: Physiopathology and Treatment with L–dopa,*" Clinical Neuropharmacology, 1986; 9:456–463.

J Montplaisir, et al., "*The Effect of Pramipexole, A D3 Preferring Agonist, on the Restless Legs Syndrome (RLS),*" Neurology, 1999; vol. 52; p. 938.

J Montplaisir, et al., "*The Effect of Pramipexole on Sensory and Motor Manifestations of the Restless Leg Syndrome,*" American Academy of Neurology, Minneapolis Convention in Minnesota, Apr. 29, 1998.

J. Montplasir, et al., "*The Treatment of the Restless Leg Syndrome With or Without Periodic Leg Movements in Sleep,*" Sleep, 1992; 15(5): 391–395.

SS Mosko, et al., "*Somatosensory and Brainstem Auditory Evoked Responses in Sleep–related Periodic Leg Movements,*" Sleep, 1986; 9:399–404.

S Noel, et al., "*Low Dosage of Pergolide in the Treatment of Restless Legs Syndrome,*" Acta Neurologica Belgica, 1998; 98 (1) 52–3.

M Oechsner, "*[Idiopathic Restless Legs Syndrome: Combination Therapy with Levodopa and * Ropinirole*],*" Aktuelle Neurologie, 1998; 25/5 (190–192).

Ondo, W, "*Ropinirole for Restless Legs Syndrome,*" Mov Disord., 1999; 1, pp. 138–140.

G Reynolds, et al., "*Restless Leg Syndrome and Rheumatoid Arthritis,*" British medical Journal, 1986; 292:659–660.

E Ruiz–Primo, *Is Nocturnal Myoclonus a Common Sleep Disturbance in Children with Leukaemia*, Dev Med Child Neurol, 1987; 29:833.

F Salvi, et al., "*Restless Legs Syndrome and Nocturnal Myclonus: Initial Clinical Manifestation of Familial Amyloid Polyneuropathy,*" J Neurol Neurosurg Psychiatry, 1990; 53:522–525.

R Sandyk, et al., "*L–Dopa in Uremic Patients with the Restless Legs Syndrome,*" Int J Neurosci, 1987; 35:233–235.

MH Silber, et al., "*Pergolide in the Management of Restless Legs Syndrome: An Extended Study,*" Sleep 1997; 20(10):878–82.

MH Silber, et al., "*Restless Legs Syndrome,*" Mayo Clinic Proceedings, 1997; 72/3 (261–264).

JS Simpson, "*Familial Akathisia and Depression Treated with Mefazodone [letter],*" Canadian Journal of Psychiatry, Revue Canadienne De Psychiatre, 1996; 41 (8) 539–40.

JD Spillane, "*Restless Legs Syndrome in Chronic Pulmonary Diseases,*" Br Med J, 1970; 4:796–798.

J Staedt, et al., "*Nightly Myoclonus Syndrome (NMS) and Restless Legs Syndrome (RLS)—Review and Case Report,*" Fortschr. Neurol. Psychiat. 62, 1994; pp. 88–93.

J Staedt, et al, "*Pergolide: Treatment of Choice in Restless Legs Syndrome (RLS) and Nocturnal Myoclonus Syndrome (NMS). Long Term Follow up on Pergolide. Short Communication,*" Journal of Neural Transmission, 1998; 105 (2–3) 265–8.

J Staedt, et al., "*Pergolide: Treatment of Choice in Restless Legs Syndrome (RLS) and Nocturnal Myoclonus Syndrome (NMS). A Double–Blind Randomized Crossover Trial of Pergolide versus L–Dopa,*" Journal of Neural Transmission, 1997; 104 (4–5) 461–8.

K Stiasny, et al., "*Cabergoline in RLS,*" ENS, Nice Abstract, 1998.

MJ Thorpy, Chairman, Diagnostic Classification Steering Committee in International Classification of Sleep Disorders: Diagnostic and Coding Manual—Table of Contents, 1990; American Sleep Disorders Association.

C Trenkwalder, et al., "*L–Dopa in Uremic and Idiopathic Restless Legs Syndrome: a double–blind, crossover trial,*" Sleep, 1995; 18:681–688.

C Trenkwalder, et al., "*Therapy of Idiopathic and Uremic Restless legs Syndrome Therapie des idiopathischen und urämischen Restless–Legs–Syndroms,*" Nervenarzt, 1996; 67 (4) 265–76, Ref: 79.

PT Trzepacz, et. al., "*Response to Opioids in Three Patients with Restless Legs Syndrome,*" Ann J Psychiatry, 1984; 141:993–995.

C Von Scheele, "*Levodopa in Restless Legs,*" Lancet, 1986; 2:426–427.

C Von Scheele, "*Long–term Effect of Dopaminergic Drugs in Restless Legs. A 2–year Follow–up,*" Archives of Neurology, 1990; 47 (11) 1223–4.

AS Walters, et al., "*A Double–blind Randomized Crossover Trial of Bromocriptine and Placebo in Restless Leg Syndrome,*" Ann Neurol, 1988; 24:455–458.

AS Walters, "*Towards a Better Definition of the Restless Legs Syndrome,*" The International Study Group, Mov Disord, 1995; 10(5):634–42.

JC Ware, et al., "*Nocturnal Myoclonus and Tricyclic Antidepressants,*" Sleep Research, 1984; 13:72.

S Watanabe, et al., "*Periodic Leg Movements During Either Epidural or Spinal Anesthesia in an Elderly Man without Sleep–related (Nocturnal) Myoclonus,*" Sleep, 1990; 13:262–266.

LR Wechsler, et al., "*Periodic Leg Movements of Sleep (Nocturnal Myoclonus): An Electrophysiological Study,*" Annals of Neurology, 1986; 19:168–173.

TC Wetter, et al., "*A Polysomnographic, Controlled Study of Pergolide in the Treatment of Restless Legs Syndrome,*" Neurology, 1998; 50(4):A69.

J Winkelman, et al., "*Treatment of Restless Leg Syndrome with Pergolide—An Open Clinical Trial,*" Mov Disord, 1998; 13(3):566–9.

USE OF PRAMIPEXOLE IN THE TREATMENT OF RESTLESS LEGS SYNDROME

FIELD OF THE INVENTION

The present invention relates to the use of pramipexole or 2-amino-6-n-propylamino-4,5,6,7-tetrahydrobenzo-thiazole or the (−)-enantiomers thereof, and the pharmacologically acceptable salts thereof, in the treatment of restless leg syndrome.

BACKGROUND OF THE INVENTION

Restless leg syndrome (RLS) is a neurosensorimotor disorder with paresthesias, sleep disturbances and, in most cases, periodic limb movements of sleep (PLMS).

Pramipexole is a dopamine-$D_3/D_2$ agonist the synthesis of which is described in European Patent 186 087 and its counterpart, U.S. Pat. No. 4,886,812. It is known primarily for the treatment of schizophrenia and Parkinson's disease. It is known from German patent application DE 38 43 227 that pramipexole lowers the plasma level of prolactin. Also, this European patent application discloses the use of pramipexole in the treatment of drug dependency. Further, it is known from German patent application DE 39 33 738 that pramipexole can be used to decrease abnormal high levels of thyroid stimulating hormone (TSH). U.S. Pat. No. 5,112,842 discloses the transdermal administration of the compounds and transdermal systems containing these active compounds. The WO patent application PCT/EP 93/03389 describes pramipexole as an antidepressant agent, while the PCT application PCT/US95/15618 discloses the neuroprotective effects of pramipexole.

Surprisingly and unexpectedly, it has been found that pramipexole and the pharmacologically acceptable salts thereof can be used in the treatment of restless leg syndrome.

SUMMARY OF THE INVENTION

The present invention particularly provides a method for treatment of restless legs syndrome in a patient suffering from or susceptible to such condition comprising the administration of an effective amount of pramipexole. By pramipexole is meant 2-amino-6-n-propylamino-4,5,6,7-tetrahydrobenzothiazole, its (−)-enantiomer thereof, and pharmacologically acceptable salts thereof especially (−)-2-amino-6-n-propylamino-4,5,6,7-tetrahydrobenzothiazole dihydrochloride ($H_2O$).

2-Amino-6-n-propyl-amino-4,5,6,7-tetrahydrobenzothiazole, particularly the (−)-enantiomer thereof, and the pharmacologically acceptable acid addition salts thereof can be given for treating RSL. The form of conventional galenic preparations consist essentially of an inert pharmaceutical carrier and an effective dose of the active substance; e.g., plain or coated tablets, capsules, lozenges, powders, solutions, suspensions, emulsions, syrups, suppositories, etc.

Preferred are tablets comprising 0.88 (0.125), 0.18 (0.25), 0.7 (1.0), 088 (1.25) and 1.1 (1.5) mg of Pramipexole base (mg Pramipexole 2HCl), respectively, and further comprising mannitol, maize starch, colloidal silica, polividone and magnesium stearate as excipients.

The effective dose range is 0.001 to 10.0 mg/day and patient, preferred between 0.001 and 6, more preferred between 0.01 to 6 and especially preferred between 0.75 and 4.5 mg/day and patient p.o. In addition to being administered by oral or intravenous route pramipexole may also be administered transdermally or by inhalation.

Dosages should be increased gradually from a starting dose of about 0.264 mg of base per day and then increased every 5–7 days. Providing patients do not experience intolerable side effects, the dosage should be titrated to achieve a maximal therapeutic effect.

DESCRIPTION OF THE PREFERRED EMBODIMENTS

The present invention is seen more fully by the examples given below:

In a pilot study on Restless Leg Syndrome, 10 patients have been treated with pramipexole in a crossover design. The patients received up to 1.5 mg a day of pramipexole over 4 weeks. After the first treatment period there is a two week wash-out period and an additional 4-week treatment period.

Since the symptoms of RLS are quite obvious, their improvement from treatment was obvious to the investigator.

We claim:

1. A method for treating restless legs syndrome in a patient suffering from or susceptible to such condition comprising the administration of an effective amount of the compound 2-amino-6-n-propylamino-4,5,6,7-tetrahydrobenzothiazole, its (−)-enantiomer thereof, and pharmacologically acceptable salts thereof.

2. A method for treating restless legs syndrome in a patient suffering from or susceptible to such condition comprising the administration of an effective amount of Pramipexole, its dihydrochoride, or its dihydrochloride-($H_2O$) thereof.

3. The method of claim 2, wherein the dose of Pramipexole is about 0.01–10.0 mg/day.

4. The method of claim 2, wherein the dose of Pramipexole is between about 0.75–4.5 mg/day.

* * * * *

UNITED STATES PATENT AND TRADEMARK OFFICE
CERTIFICATE OF CORRECTION

PATENT NO : 6,001,861
DATED : December 14, 1999
INVENTOR(S): WH Oertel, D. Meier, B. Gomez-Mancilla, J Montplaisir It is certified that error appears in the above-identified patent and that said Letters Patent are hereby corrected as shown below:

Assignees should read:
Pharmacia & Upjohn Company, Kalamazoo, Mich.; Boehringer Ingelheim Pharma KG, Ingelheim, Fed. Rep. of Germany Signed and Sealed this First Day of May, 2001

Attest:

NICHOLAS P. GODICI

*Attesting Officer*  *Acting Director of the United States Patent and Trademark Office*